United States Patent [19]

Jinkerson

[11] Patent Number: 5,662,707
[45] Date of Patent: Sep. 2, 1997

[54] POLYMERIZABLE YELLOW DYES AND THEIR USE IN OPHTHALMIC LENSES

[75] Inventor: David L. Jinkerson, Fort Worth, Tex.

[73] Assignee: Alcon Laboratories, Inc., Fort Worth, Tex.

[21] Appl. No.: 667,347

[22] Filed: Jun. 21, 1996

Related U.S. Application Data

[63] Continuation of Ser. No. 445,809, Jul. 5, 1995, abandoned, which is a continuation of Ser. No. 138,663, Oct. 18, 1993, Pat. No. 5,470,932.

[51] Int. Cl.$^6$ .......................... A61F 2/16; C08F 226/02; C08F 220/10
[52] U.S. Cl. .......................... 623/6; 526/312; 526/328.5
[58] Field of Search .......................... 623/6; 526/312, 526/328.5

[56] References Cited

U.S. PATENT DOCUMENTS

| | | | |
|---|---|---|---|
| 3,190,860 | 6/1965 | Fertig et al. | 260/80.5 |
| 4,573,998 | 3/1986 | Mazzocco | 623/6 |
| 4,619,657 | 10/1986 | Keates et al. | 623/6 |
| 4,619,662 | 10/1986 | Juergens, Jr. | 623/6 |
| 4,795,461 | 1/1989 | Lindqvist et al. | 623/6 |
| 4,863,466 | 9/1989 | Schlegel | 623/6 |
| 4,878,748 | 11/1989 | Johansen et al. | 351/44 |
| 5,047,447 | 9/1991 | Gallas | 523/106 |

FOREIGN PATENT DOCUMENTS

| | | |
|---|---|---|
| 0 259 532 | 3/1988 | European Pat. Off. . |
| 0 359 829 | 3/1990 | European Pat. Off. . |
| 6 0202-110-A | 10/1985 | Japan . |
| 1-299560 | 12/1989 | Japan . |
| 3-57629 | 3/1991 | Japan . |
| 3-128060 | 5/1991 | Japan . |
| 1516111 A1 | 10/1989 | U.S.S.R. . |
| WO 89/03386 | 4/1989 | WIPO . |
| WO 91/01696 | 2/1991 | WIPO . |

OTHER PUBLICATIONS

J. T. Guthrie, Rev. Prog. Coloration 20, 40–52, 1990.
J. T. Guthrie, "Polymeric Colorants", Rev. Prog. Coloration 20, 40–52, 1990.
Ham, Jr. et al., "Retinal effects of blue light exposure," *SPIE vol. 229 Ocular Effects of Non–ionizing Radiation*, 46–50 (1980).
Ham, Jr., "Ocular Hazards of Light Sources: Review of Current Knowledge," *Journal of Occupational Medicine*, vol. 25(2), 101–103 (1983).
Hovis et al., "Physical Characteristics and Perceptual Effects of Blue–Blocking Lenses," *Optometry & Vision Science*, vol. 66(10), 682–689 (1989).
Lerman et al., "Spectroscopic Evaluation and Classification of the Normal, Aging, and Cataractous Lens," *Ophthal. Res.* vol. 8, 335–353 (1976).
Nilsson et al., "Does a blue light absorbing IOL material protect the neuro–retina and pigment epithelium better than currently used materials?", *Lasers and Light in Ophthalmology*, vol. 3(1), 1–10 (1990).
Zigman, "Tinting of Intraocular Lens Implants," *Arch Ophthalmol*, vol. 100, 998 (1982).

Primary Examiner—Joseph L. Schofer
Assistant Examiner—Wu C. Cheng
Attorney, Agent, or Firm—Patrick M. Ryan

[57] ABSTRACT

Novel polymerizable yellow dyes are disclosed. Additionally, novel and known dyes are used to block or lower the intensity of blue light transmitted through ocular lenses and other windows.

8 Claims, 3 Drawing Sheets

POLYMERIZABLE YELLOW DYES AND THEIR USE IN OPHTHALMIC LENSES

This application is a continuation of application Ser. No. 08/445,809, filed on Jul. 5, 1995, now abandoned, which is a continuation of Ser. No. 08/138,663, filed on Oct. 18, 1993, now U.S. Pat. No. 5,470,932.

FIELD OF THE INVENTION

This invention relates to polymeric yellow dyes and their use in ophthalmic lenses. In particular, this invention relates to polymerizable yellow dyes of the azo family in "blue-blocking" ophthalmic lenses.

BACKGROUND OF THE INVENTION

The assessment of optical hazards in recent years has lad to the recognition of the possible hazards to the retina associated with blue light (400–500 nm). If the blue light hazard is a real threat to vision, then the UV/visible transmission characteristics of ophthalmic lenses, and intraocular lenses (IOLs) in particular, should be modified to provide adequate protection from blue light hazards encountered in the environment.

In the ambient environment solar radiation is the primary hazard to vision. The sun freely emits UV, visible and IR radiation much of which is absorbed by the atmosphere. The solar radiation that is transmitted through the atmosphere and reaches the earth's surface consists of UV-B radiation (230–300 nm), near UV or UV-A, radiation (300–400 nm), visible light (400–700 nm) and near IR radiation (700–1400 nm). The ocular media of man in its normal, healthy state freely transmits near IR and most of the visible spectrum to the retina, but UV-B radiation is absorbed by the cornea and does not reach the retina. The transmission of near UV and the blue portion of the visible spectrum can be absorbed by the crystalline lens depending on age.

The human crystalline lens changes its UV and visible transmission characteristics as it ages. In infancy the human lens will freely transmit near UV and visible light above 300 nm, but with further aging the action of UV radiation from the environment causes the production of yellow pigments, fluorogens, within the lens. By age 54 the lens will not transmit light below 400 nm and the transmission of light between 400 and 500 nm is greatly diminished. As the lens ages it continuously develops a yellow color, increasing its capacity to filter out near UV and blue light. Therefore, after cataract removal the natural protection provided by the aged human lens is also removed. If the cataract is replaced by an IOL, usually UV protection is provided, but blue light protection is still lacking.

The use of conventional yellow dyes, such as commercially available 4-phenylazophenol (Solvent Yellow 7), 2-(2'-methyl)-phenylazo-4-methyl phenol (Solvent Yellow 12) and N-(4-phenylazo)phenyl diethanol amine (Solvent Yellow 58), in IOLs to block blue light is not desirable because these dyes are not bound to the lens material and thus may leach out of the IOL after it is inserted in the eye. These non-bonded dyes also cause problems in the manufacture of polymer lenses that are extracted with a solvent after they are formed. In this extraction step, the solvent may remove up to 90% of the non-bonded dye from the lens.

Japanese Kokai Patent Application No. Hei 1[1989]-299, 560 ("Menikon Application") claims an intraocular lens material characterized by a polymerizable ultraviolet light absorber having a polymerizable group selected from an acrylol group, a methacrylol group, a vinyl group, an allyl group, and an isopropenyl group, and a polymerizable dye having a polymerizable group selected from an acryloyl group, an allyl group, and an isopropenyl group, which are copolymerized with other polymerizable lens-forming monomer components. Also taught by the Menikon Application are polymerizable dyes having a polymerizable group selected from methacryloyl groups, vinyl groups, and acryl groups. The Menikon Application lists numerous formulas representing hundreds of dyes. As examples of the polymerizable dyes of the azo system, the Menikon Application lists those of the general formula:

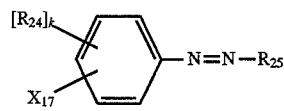

Structure VI where $X_{17}$ may be, among others, any of the groups represented by:

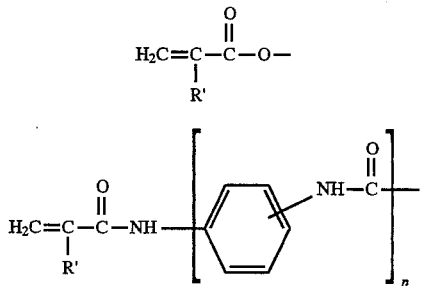

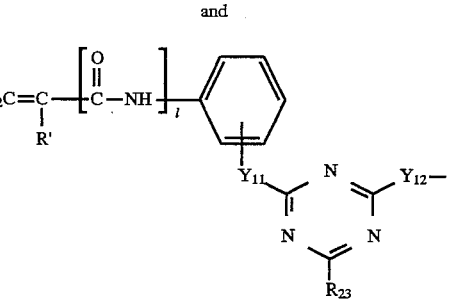

and $R^1$ is —H or —CH$_3$;
$R_{23}$ may be, among others, —H, —OH, or a halogen atom;
$R_{24}$ may not be H, but may be —OH, —CH$_3$, —C$_2$H$_5$, —OCH$_3$, —OC$_2$H$_5$, and halogen atoms;
k, m, l, and n are integers of 0 or 1;
$R_{25}$ may be, among others, a benzene derivative substituted with $C_1$–$C_8$ alkyl groups;
$R_{26}$ is —H, or $C_1$ to $C_3$ lower alkyl; and
$Y_{11}$ and $Y_{12}$ are —NH— or —O—.

The azo dyes taught in the Menikon Application suffer the following disadvantages, however. Directly attaching reactive acrylic/methacrylic groups or other electron-withdrawing groups, such as carbonyl, carboxylic acid, or ester groups, to the dye moiety weakens dye strength and may change dye color.

The effect of electron-withdrawing groups on the color and relative strength of a yellow dye can be quite pronounced. For example, the yellow dye known as Solvent Yellow 58 is converted into a red dye, Pigment Red 100, solely by the addition of a carboxylic acid group directly bonded to the phenylazophenyl dye moiety.

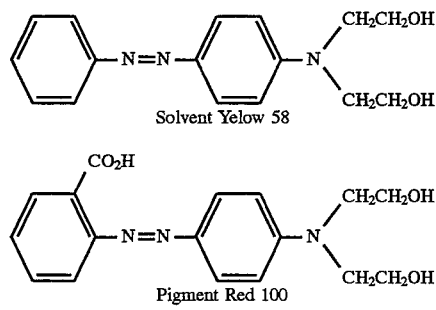

There is only one case in which the Menikon Application allows an acrylic/methacrylic group not directly bound to the azo dye moiety by an electron-withdrawing group. This case requires instead that an amino group be directly attached to the dye moiety. Even though amino azo dyes are useful, they are less desirable than phenolic azo dyes because the amino group accelerates the decomposition of peroxide initiators, such as those used in conventional free-radical polymerization processes.

Another example of dyes based on the amino azo system are the polymeric colorants based on acrylated chromophores of the type

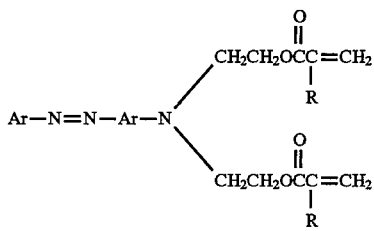

wherein R=CH$_3$ or H; and the Ar group is phenyl, naphthyl, etc. Guthrie, "Polymeric Colorants," *Rev. Prog. Color Relat. Topics*, Vol. 20, 40–52 (1990). Substituents may be added to the aromatic groups to provide variations in color and other physical properties. The works of various people am summarized in this review article. Some of the work reviewed includes reactive azo dyes containing methacrylate, acrylate, epoxide and vinyl ester functionalities in the following applications and studies: optical recording materials, the non-linear optical susceptibility of copolymers containing acrylic azo monomers and methyl methacrylate, and the determination of copolymerization parameters and reactivity ratios for the copolymerization of azo dye monomers containing a methacryloyl functionality with styrene and with methyl methacrylate.

What is needed are additional polymerizable yellow dyes which are easily synthesized from commercially available dyes or other starting materials and which, when incorporated in ophthalmic lenses, will not be extracted out of the lens during solvent extraction or leach out of the lens after insertion in the eye.

SUMMARY OF THE INVENTION

The polymerizable yellow dyes of the invention are soluble in organic monomers, such as acrylic/methacrylic monomers, and contain in their chemical structure one or more acrylic or methacrylic functional groups which are reactive towards free radical polymerization. These dyes, when polymerized with organic monomers capable of forming a transparent material, will be bonded to the polymer and thus greatly reduce the amount of dye which can leach out of the material. As a result, these dyes can be used in transparent materials to decrease the intensity of blue light transmitted through them. These transparent materials with one or more of the bondable yellow dyes incorporated in them may be extracted with organic solvents to remove unreacted monomers, low molecular weight oligomers and low molecular weight polymers, as well as other impurities, and then used to make ocular lenses such as intraocular lenses (IOLs), contact lenses, eyeglasses and other windows. These transparent materials containing yellow dye may also be used to make lens coating materials.

Although like compounds can be expected to copolymerize more efficiently than unlike compounds, it has now been found that polymerizable yellow dyes having one or more polymerizable acrylate or methacrylate groups which have been copolymerized with one or more lens-forming acrylate or methacrylate monomers are much more efficiently incorporated into the polymeric lens materials than yellow dyes having other types of polymerizable groups, such as vinyl groups.

Additionally, it has now been found that polymerizable yellow dyes of the azo family which do not contain electron-withdrawing groups directly attached to the dye moiety are much stronger yellow dyes than those which do. Acrylic/methacrylic yellow dyes which do not have the polymerizable group directly bonded to the dye moiety are therefore stronger than those which do.

DETAILED DESCRIPTION OF THE INVENTION

Figure 1:
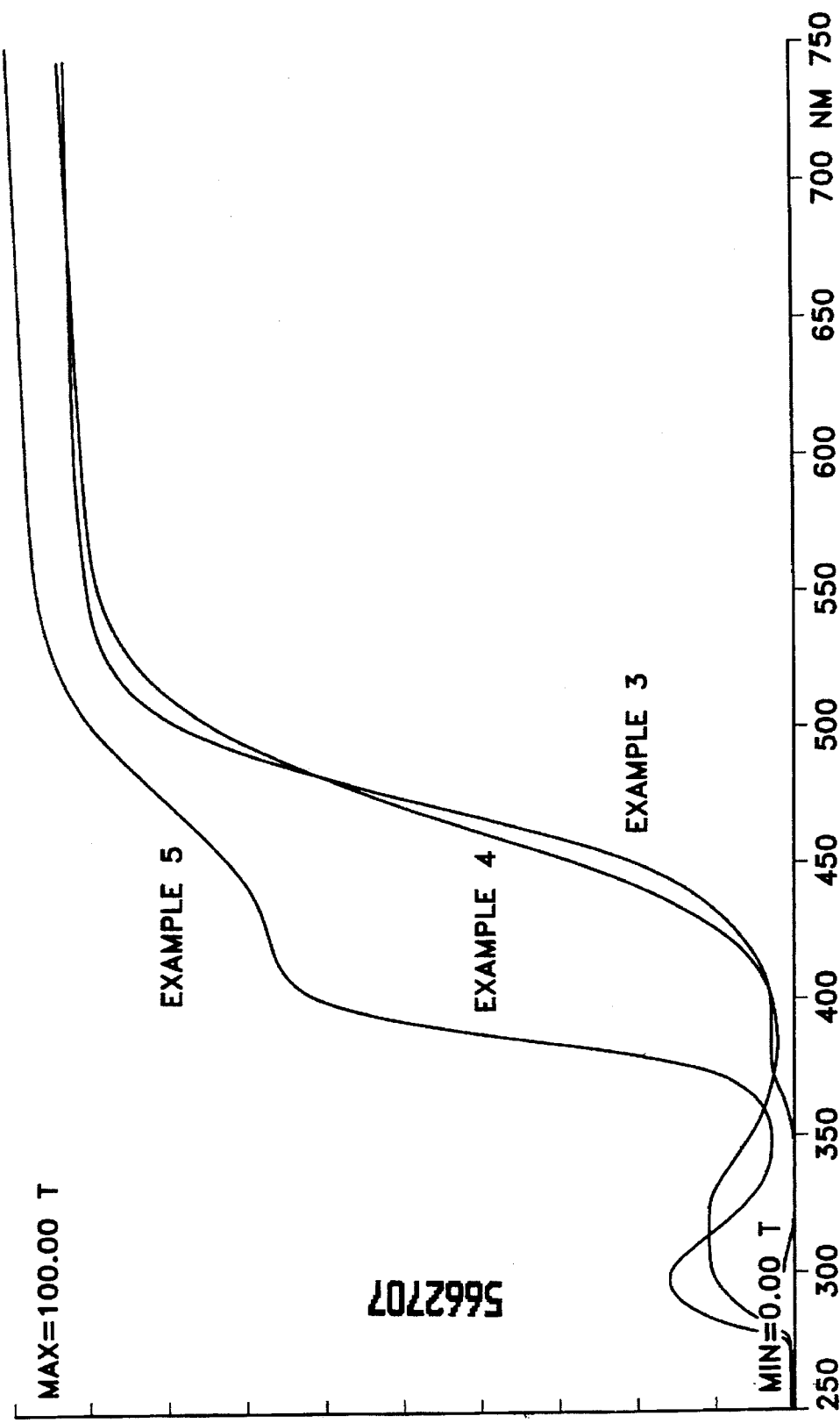
FIGS. 1 and 2 show the transmittance of acrylic/methacrylic ophthalmic lens materials containing various yellow dyes.

The polymerizable yellow dyes of the present invention am based on the azo dye system and contain polymerizable acrylate/methacrylate groups, These dyes am characterized by a spacing group which separates the polymerizable acrylate/methacrylate group from the dye moiety. These dyes are further characterized by the absence of an electron-withdrawing group directly attached to the dye moiety.

As used herein, "dye moiety" refers to the portion of the dye molecule primarily responsible for causing the dye's intense color. In this invention, the dye moiety is thus the phenyl-azo-phenyl (Ph-N=N-Ph) portion of the polymerizable yellow dye structure.

The spacing groups of this invention may be any group which separates, by means of covalently bonded atoms, the dye moiety from the polymerizable acrylic/methacrylic group. The sparing group separates the dye moiety from the acrylic/methacrylic group in such a way as to minimize the effect of the acrylic/methacrylic group on dye strength and color. The minimum effect on dye strength and color is achieved by directly attaching the sparing group to the dye moiety with a non-electron-withdrawing residue.

Preferred sparing groups of the present invention are those of the formula:

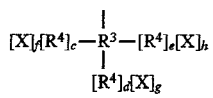

immediately preceding $[X]_f$ and immediately following both $[X]_g$ and $[X]_h$, where $R^3$ is directly attached to the dye moiety and consists of an alkyl group of up to 6 carbon atoms;

$R^4$ is an acylic organic spacing group of up to 10 atoms which is composed of carbon, hydrogen, silicon, oxygen, nitrogen, phosphorous, sulfur, chloride, bromine, or fluorine alone or in any combination;

X=O, NH, $NR^5$;

$R^5=C_1$ to $C_{10}$ alkyl;

d, e, g, and h independently=an integer from 0 to 4; and c and f independently=an integer from 1 to 4.

Electron-withdrawing groups am not permitted to be covalently bonded to the dye moiety because they can weaken the strength of the yellow dye and, in some cases, change the absorption nature of the dye sufficiently to cause a change in color. Examples of electron-withdrawing groups which are not permitted to be directly attached to the dye moiety include carbonyl groups, such as those found in ketones; carboxylic acid esters; amides; imines; immidies; imminic add esters (especially analogues derived from 1,3, 5-triazeno systems); ureas; urethanes; and so on.

The novel dye compounds of the present invention include acrylates/methacrylates of the formula:

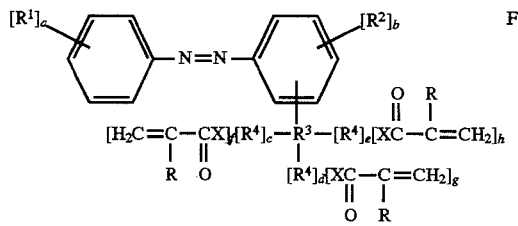

Formula 1 wherein

R=H or $CH_3$;

$R^1$=H, $C_1$ to $C_{20}$ alkyl, $OCH_3$, $OC_2H_5$, $OC_3H_7$, or $OC_4H_9$;

a and b independently=the integer 1 or 2;

$R^2=R^1$, OH, $NH_2$, $NHR^5$, $N(R^5)_2$, SH, $SR^5$, $OR^5$, OSi$(R^5)_3$, or Si$(R^5)_3$; and $R^3$, $R^4$, $R^5$, X, C, d, e, f, g and h are as defined above.

The preferred compound of Formula 1 is N-2-[3-(2'-methylphenylazo)-4-hydroxyphenyl]ethyl methacrylamide:

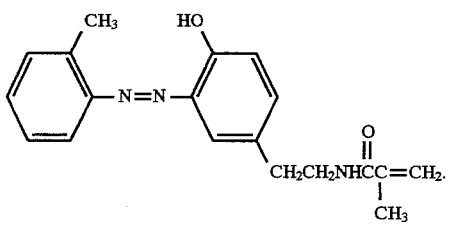

Compound 1

Compounds of Formula 1 may be prepared by staring with a phenolic, aniline, or other substituted benzene compound containing an organic spacing group terminated by one or more amino or hydroxyl moieties. One skilled in the art could form a reaction with methacrylic anhydride, acrylic anhydride, acryloyl chloride, methacryloyl chloride or other suitable acrylic/methacrylic reagent to give an intermediate acrylic/methacrylic compound. If necessary to induce the reactivity of the side chain amino or hydroxyl group, strong bases, such as sodium hydride or butyl-lithium, may be employed; weaker bases, such as triethylamine, may also be useful.

The intermediate acrylic/methacrylic compound may then be azo-coupled with an appropriate diazonium salt to yield the reactive azo yellow dyes of Formula 1. Such azo coupling reactions are performed in two stages. In the first stage, an appropriate aniline compound (optionally substituted) is converted into a reactive diazonium salt at low temperatures, such as 0° to 10° C., by reaction with sodium or other suitable nitrite salt in aqueous solution at about pH 2. In the second stage, the reactive diazonium salt is then azo-coupled with the intermediate acrylic/methacrylic compound described above to form the desired azo product. The azo coupling of phenolic compounds proceeds best at a solution pH of about 4 to 8. However, with increasing reaction pH, the diazonium salt has a tendency to form byproducts via side reactions. These side reaction products are also phenolic compounds which can compete with the desired intermediate acrylic/methacrylic compound in the azo coupling reaction. As a result, changing the reaction stoichiometry from a 1:1 molar equivalence to a 4:1 excess of diazonium salt to acrylic/methacrylic intermediate compound is the preferred way to synthesize Compound 1. Other reaction stoichiometries may be more effective in the azo coupling of other acrylic/methacrylic phenolic intermediates as determined by someone skilled in the art.

In the case of Compound 1, tyramine [4-(2-aminoethyl) phenol] acts as the phenolic starting material. It is reacted with methacrylic anhydride without catalytic base being necessary to give the intermediate compound containing the reactive acrylic/methacrylic moiety, 4-(2-methacrylamidoethyl)phenol. The azo coupling reagent is then prepared by reacting ortho-toluidine (2-methylaniline) at about 0° C. and pH 2 with sodium nitrite in the presence of 6N hydrochloric acid. This produces the reactive diazonium salt of ortho-toluidine. This diazonium salt is then reacted in situ with the phenoxide of the intermediate compound, 4-(2-methacrylamidoethyl) phenol, by azo coupling to give the preferred compound of Formula 1, Compound 1.

Also included within the scope of the present invention are the diacrylates/dimethacrylates of the formula:

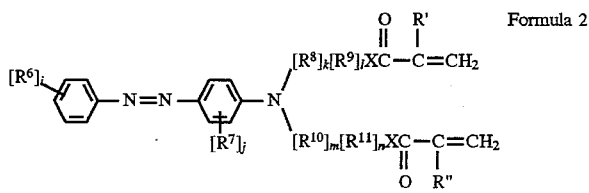

Formula 2 wherein

R' and R" independently=H or $CH_3$;

$R^6$ and $R^7$ independently=$R^1$;

i and j independently=the integer 1 or 2;

$R^8$, $R^9$, $R^{10}$ and $R^{11}$ independently=$R^4$;

k and m independently=an integer from 1 to 6;

l and n independently=an integer from 0 to 6;

x=O, NH, $NR^5$; and $R^5=C_1$ to $C_{10}$ alkyl.

The preferred compound of Formula 2 is N,N-bis-(2-methacroylethyl)-(4-phenyl-azo)aniline:

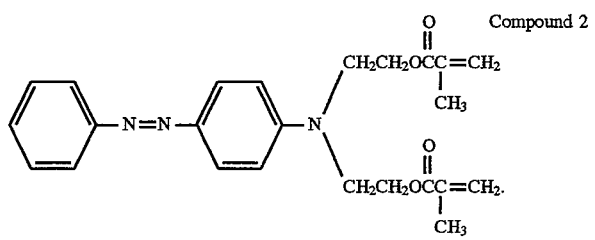

Compound 2

Compound 2 may be prepared by the azo coupling reaction of aniline (optionally substituted) with N-phenyldiethanolamine under conditions described above for azo coupling reactions, except that only a 1:1 stoichometry is necessary for azo coupling of N-phenylamines with diazonium salts. The azo coupling proceeds well at a pH of about 2 to 4. The diazonium salt of aniline is reacted in-situ with N-phenyldiethanolamine to give the intermediate azo dye N-(4-phenylazo)phenyl diethanolamine (also known as Solvent Yellow 58). The dimethacrylate derivative can then be prepared by reacting the intermediate azo dye, N-(4-phenylazo)phenyl-diethanolamine with methacrylic anhydride in the presence of a weak base, such as triethylamine, to yield the reactive dimethacrylic azo yellow dye, N-(4'-phenylazo)phenyl-2-bis-(2-methacrylo)ethylamine. In addition, other stronger bases, such as sodium hydride or butyllithium, might be used to form the disodium or dilithium salt followed by reaction with methacrylic anhydride, or other methacrylic/acrylic agent used to incorporate the polymerizable group.

As one skilled in the art would appreciate, other compounds of Formula 2 may be prepared using analogous reaction sequences and corresponding starting materials. In general, compounds of Formula 2 may be prepared by azo coupling aniline (optionally substituted) with a variety of N-phenylamines having two pendant organic spacing groups attached to the amine functionality. The organic spacing groups contain hydroxy or amino residues to which acrylic/methacrylic functional groups may be bonded.

The yellow polymerizable dyes of the present invention may be incorporated in a number of materials in a variety of applications where it is desirable to block blue light (approximately 400–500 nm.). Such applications may include, for example, contact lenses, eyeglasses and sunglasses. A preferred application is the use of yellow polymerizable dyes in intraocular lenses. As such, one embodiment of the present invention is an intraocular lens containing one or more polymerizable yellow dyes ("blue-blocking IOLs").

The blue-blocking IOLs of this invention may be made by co-polymerizing one or more lens-forming monomers with one or more polymerizable yellow dyes of Formula 1 or 2. In a preferred embodiment, these monomers are cured directly in a polypropylene mold so that a finished optic is produced. The time and temperature for curing vary with the particular lens-forming material chosen. The optic may be combined in a number of known ways with a variety of known haptics to produce an IOL.

The total mount of yellow dye used to form a blue-blocking IOL is typically less than about 1 wt. %. Preferably, the total amount of yellow dye is less than about 0.25 wt. %, and most preferably, the total amount of yellow dye is less than about 0.1 wt. %.

Suitable lens-forming monomers for use in the present invention include methyl methacrylate, 2-hydroxyethyl acrylate, 2-hydroxyethyl methacrylate, 3-hydroxypropyl acrylate, 3-hydroxypropyl methacrylate, n-vinyl pyrolidone, styrene, eugenol (4-hydroxyvinyl benzene), α-methyl styrene. In addition, for high-refractive index foldable lens applications, suitable monomers include, but am not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate; 2-(4-(1-methylethyl)phenyl ethyl methacrylate, 2-(4-methoxyphenyl)ethyl methacrylate, 2-(4-cyclohexylphenyl) ethyl methacrylate, 2-(2-chlorophenyl)ethyl methacrylate, 2-(3-chlorophenyl)ethyl methacrylate, 2-(4-chlorophenyl) ethyl methacrylate, 2-(4-bromophenyl)ethyl methacrylate, 2-(3-phenylphenyl)ethyl methacrylate, 2-(4-phenylphenyl) ethyl methacrylate), 2-(4-benzylphenyl)ethyl methacrylate, and the like, including the corresponding methacrylates and acrylates. N-vinyl pyrolidone, styrene, eugenol and G-methyl styrene may also be suitable for high-refractive index foldable lens applications. A preferred lens-forming monomer mixture is the mixture of 2-phenylethyl methacrylate (PEMA) and 2-phenylethyl acrylate (PEA).

The copolymerizable cross-linking agent used in the lens-materials of this invention may be any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is 1,4-butanediol diacrylate (BDDA).

Suitable crosslinkers also include polymeric crosslinkers, such as, Polyethylene glycol 1000 Diacrylate, Polyethylene glycol 1000 Dimethacrylate, Polyethylene glycol 600 Dimethacrylate, Polybutanediol 2000 Dimethacrylate, Polypropylene glycol 1000 Diacrylate, Polypropylene glycol 1000 Dimethacrylate, Polytetramethylene glycol 2000 Dimethacrylate, and Polytetramethylene glycol 2000 Diacrylate.

An ultra-violet absorbing material can also be included in the polymeric lenses of this invention in order that the lenses may have an ultraviolet absorbance approximately equivalent to that of the natural lens of the eye. The ultraviolet absorbing material can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'methyl phenyl) benzotriazole, also known as ortho-methallyl TinUVin P ("oMTP").

Since many ultraviolet absorbing compounds have phenolic substituents or residues within their structure that are known to inhibit polymerization, the less ultraviolet absorbing compound needed the better. Reducing the concentration of such ultraviolet absorbing compounds can be beneficial to the lens forming process. When the ultraviolet absorbing compound is oMTP, it is typically present in a concentration of approximately 1.8 wt. %. However, depending on the specific yellow dye chosen and the desired transmission at a given wavelength, considerably less than 1.8 wt. % of oMTP may be required to block the transmission of ultraviolet and blue light. The same is true for other ultraviolet absorbing compounds: the use of a yellow dye in conjunction with an ultraviolet absorbing compound requires less of the ultraviolet absorbing compound than the use of the ultraviolet absorbing compound alone. The total amount of both ultraviolet absorbing compound and polymerizable yellow dye required in the IOL monomer mixture to effectively block light of about 500 nm and below may be less than 1.9 wt. %. In some cases, depending on the specific ultraviolet absorbing compound and yellow dye chosen, the total amount may be considerably less than about 1.9 wt. %.

The lens materials of this invention are prepared by generally conventional polymerization methods. A mixture of lens-forming, ultraviolet absorbing and blue light blocking monomers in the desired proportions together With a conventional thermal free-radical initiator is prepared. The mixture can then be introduced into a mold of suitable shape to form the lens, and the polymerization carded out by gentle heating to activate the initiator. Typical thermal free radical initiators include peroxides, such as benzyl peroxide, peroxycarbonates, such as bis-(4-t-butulcyclohexyl) peroxydicarbonate, azonitriles, such as azo-bis-(isobutyronitrile) (AIBN), and the like. A preferred initiator is bis-(4-t-butylcyclohexyl peroxydicarbonate) (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization. Photosensitizers can be introduced as well to permit the use of longer wavelengths; however, in preparing a polymer which is intended for long residence within the eye, it is generally preferable to keep the number of ingredients in the polymer to a minimum to avoid the presence of materials which might leach from the lens into the interior of the eye.

The polymerizable yellow dyes of this invention may also be used in lens coatings. Such coatings are produced by polymerizing the monomeric dyes of this invention with soluble polymers and casting them onto transparent materials. After coating and evaporation of the polymer solvent, such polymer solutions would impart a yellow film onto the transparent material and give the material blue light protective properties. Also, the polymerizable yellow dyes of this invention can be dissolved into a suitable monomer formula, cast onto a transparent material, and cured by a suitable free-radical initiation procedure, such as exposure to heat or UV radiation. A common technique for casting such polymer or monomer solutions might include the spin casting technique for applying thin films to surfaces.

The polymerizable yellow dyes of this invention might also be dissolved into a suitable solvent or monomer formula, followed by immersion of the transparent material into the dye solution. The transparent material would then imbibe the dye into its matrix by absorbing the solution and swelling. The curing of the polymerizable dyes can be accomplished by heat, radiation or other means suitable to bond the dye into the polymer.

The invention will be further illustrated by the following examples which are intended to be illustrative, but not limiting.

EXAMPLE 1

Preparation of Compound 1

Step one: Synthesis of Compound 1 Precursor

Into a reaction flask was added 4.4834 g (32.68 mmoles) of tyramine and 100 mL of methanol. The tyramine was dissolved with stirring and sonnication. To the reaction flask was added 5.089 g (33.01 mmoles) of methacrylic anhydride (MAA) dropwise with constant stirring. The reaction was performed at room temperature and was monitored by high performance liquid chromatorgraphy (HPLC). Within the first hour after the MAA addition, the reaction was completed.

To the reaction flask was added 100 mL of 10% Aq. NaCl and an additional 30 g of salt was added to the flask. The excess salt was filtered off and the reaction flask was cooled overnight in a freezer. The next morning a white solid precipitate was filtered from the reaction solution and was washed with cold 50:50 methanol:water solution. The liquid supernatent was cooled again to obtain a second crop of crystals. After filtering the second crop, all the solid precipitant was combined together and 5.6668 g (27.61 mmoles) of Compound 1 precursor product was obtained, Yield=84.5%.

The product was recrystallized from $CHCl_3$. The solid product was filtered off, dried in air and had a melting point of 123° C. The MP for tyramine starting material is 161°–163° C. The Compound 1 precursor product identity was confirmed by comparison of FTIR, NMR and mass spectrum data to that of the tyramine starting material.

Step two: Synthesis of Compound I from the Compound I Precursor

Into a 1000 mL beaker was added 200 mL of deionized water followed by 6.2 g (100 mmoles) of boric acid ($H_3BO_3$). The boric acid was dissolved with stirring and the pH was monitored with the aid of a Orion EA940 Ion Analyzer and a Ross pH electrode. To the beaker was added dropwise 6N HCl to adjust the solution to about pH 2. o-Toluidine in the amount of 2.0831 g (19.94 mmoles) was added to the beaker and the solution pH was again adjusted to pH 2 with the addition of 6N HCl. Ice was added to the reaction solution to cool it down to 0°–10° C.

Into a separate beaker was weighed 1.3603 g (19.71 mmoles) of sodium nitrite, $NaNO_2$ and 20 mL of water. The sodium nitrite solution was added dropwise into the reaction solution with constant stirring and monitoring of the solution pH. The pH of the reaction was maintained at about 1.9 to 2.2 by the addition of 6N HCl. Ice was added periodically to the reaction to keep the temperature at 0°–10° C. and the reaction was stirred for about 10 minutes.

Into another beaker was placed 1.0048 g (4.90 mmoles) of Compound 1 precursor, 30 mL of water and 1.96 mL of 2.5N NaOH (4.90 mmoles) solution. This solution was added dropwise into the ice-cooled reaction solution with constant stirring. The reaction solution began to develop a light yellowish-green color which grew more intense as more of the Compound 1 precursor solution was added. The reaction solution was allowed to stir at 0°–10° C. for about 15 minutes at pH 2.0–2.5.

A 2.5N NaOH solution was added in small aliquots to the reaction solution to bring the pH up to about 8.5. With increasing pH the yellow color of the reaction solution grew brighter. The reaction solution was allowed to warm up to room temperature over about 2–3 hour time interval. As the solution warmed up a red solid floated on top of the solution and the reaction began to take on an orange color. At this point the total reaction volume was about 900 mL. Upon warming to room temperature the reaction solution darkened to a red-brown color and a very dark solid. floated on the surface of the solution. To the solution was added 14.2 g (100 mmoles) of dibasic sodium phosphate. To the reaction solution was added 6N HCl dropwise until the pH was adjusted to about 6.0.

The dark precipitate from the reaction solution was filtered off and was combined with solid skimmed from the reaction solution. The solid red product was washed with about 400 mL of ice water and air dried on the filter for about 20–30 minutes. From the reaction 6.1219 g of the red solid was obtained.

HPLC analysis of the red solid indicated that the reaction had three products. The products were separated by column chromatography using a silica gel column. The column was eluted with methylene chloride ($CH_2Cl_2$) and acetonitrile (MeCN) mobile phases. Fractions of various colored bands were collected as they eluted off the column and analyzed by HPLC. Fractions whose chromatograms indicated similar composition and purity were combined. These combined fractions were separately filtered through a 0.5 μm filter via a glass syringe into separate round bottomed flasks. The flasks containing the combined fractions were sequencially placed onto a rotary evaporator and the solvents removed under vacuum with low heating (approx. 50° C.). Upon solvent removal the products from the combined fractions remained. The flasks containing desired products were tided at 50° C. under vacuum. The combined fractions of pure product were re-analyzed by HPLC and also analyzed by mass spectroscopy and NMR spectroscopy to confirm its identity. Less pure fractions were purified by repeated column chromatography runs in the same manner as the above run until the desired product purity (>95%) was obtained.

The melting range of the product was 157°–160° C. and the amount of pure Compound 1 product obtained was 0.5153 g (1.60 mmoles), Yield=32.7%.

EXAMPLE 2

Preparation of Compound 2

Step one: Synthesis of Compound 2 Precursor by the Azo Coupling of Aniline with N-Phenyldiethanolamine Into a 1000 mL beaker was added 200 mL of water and 14.2 g (100 mmoles) of sodium phosphate, dibasic ($Na_2HPO_4$) followed by the addition of 6N HCl solution to adjust the reaction solution to pH 2. After the phosphate buffer salt was completely dissolved, 4.7351 g (50.84 mmoles) of aniline was added to the reaction solution. Ice was added to the reaction solution to cool it down to 0° C.

Into a separate beaker, 3.5151 g (50.94 mmoles) of sodium nitrite, $NaNO_2$, was dissolved in 20 mL of water. Ice was added to cool the solution. The sodium nitrite solution was added dropwise with constant stirring to the reaction solution while constantly monitoring the pH of the reaction using a Orion EA940 Ion Analyzer and a Ross pH Electrode. The pH of the reaction was maintained to about 1.9 to 2.2 by the addition of 6N HCl. After the addition of sodium nitrite solution was completed more ice was added to the reaction to keep the temperature at 0°–10° C. and the reaction was stirred for about 15 minutes.

Into another beaker was placed 9.1481 g (50.48 mmoles) of N-Phenyldiethanolamine, 100 mL of water, and enough 6N HCl was added to dissolve the solid. The N-Phenyldiethanolamine solution was added dropwise into the stirring reaction solution which was kept at 0°–10° C. by periodic addition of ice. Immediately the reaction solution began to develop a dark red to purple color which grew more intense as more of the N-Phenyldiathanolamine solution was added. After the addition was completed the solution was stirred for about an hour and warmed up to about 10° C. Then 50% w/v and 2N NaOH solutions were added to the reaction solution to pH 6.9. As the pH of the reaction solution rose, a dark red solid precipitated out of solution. At this point the total reaction volume was about 1 L. The solid was filtered off and washed with water. 27.7363 g of wet precipitate was obtained.

The solid obtained from the reaction was recrystallized from a methanol:water 91:9 solution. The Compound 2 precursor product crystals were filtered off and dried under vacuum overnight at 50° C. The identity of the Compound 2 precursor was confirmed by NMR and mass spectroscopic analysis. Compound 2 precursor in the amount of 11.1449 g (39.06 mmoles) was obtained, melting range 136°–138° C., Yield=77.4%.

Step two: Synthesis of Compound 2 by the Reaction of Compound 2 Precursor with Methacrylic Anhydride Into a 100 mL round bottomed flask was placed 1.4299 g (5.011 mmoles) of Compound 2 precursor and 25 mL of tetrahydrofuran (THF), completely dissolving the Compound 2 precursor. Into a tared 16×125 mm testtube was weighed 1.5549 g (10.086 mmoles) of MAA. The MAA was then added dropwise to the mining reaction solution using a transfer pipet and the time of MAA addition was noted. An HPLC analytical method was used to monitor the progress of the reaction with time. After about four hours, 1.0452 g (10.329 mmoles) of triethylamine (Et3N) was added dropwise to the reaction solution. The reaction was stirred for 2 days, and then another aliquot of 4.1877 g (41.385 mmoles) of $Et_3N$ was added to the reaction. The next day, the reaction was analyzed by HPLC and another aliquot of methacrylic anhydride, 3.5542 g (23.054 mmoles), was added to the reaction to complete the conversion of the Compound 2 precursor to Compound 2 product.

The crude Compound 2 product was purified by column chromatography using the same procedure as described above for Compound 1, except that lower heating was used for the solvent removal (30° C. instead of 50° C.). Less pure fractions and the remainder of the solid red product from the reaction were purified by repeated column chromatography runs in the same manner as the above run until the desired product purity was obtained. The identity of the Compound 2 product was confirmed by mass spectroscopy and NMR spectroscopy.

Compound 2 is a red gum solid at room temperature and atmospheric pressure. The residual products of three synthetic attempts were combined and purified by column chromatography. From this 1.701 g (4.04 mmoles) of pure Compound 2 product was obtained from a total of 6.25 g (21.94 mmoles) of Compound 2 precursor starting material, Yield=16.4%.

EXAMPLES 3–5

Preparation of Lens Material

The bondable yellow dyes of Examples 1 and 2, were weighed into individual test tubes. An appropate amount of a solution of monomers containing 66% PEA, 30.5% PEMA, and 3.3% BDDA by weight respectively, was added to each test tube to give a bondable yellow dye concentration of approximately 0.1% by weight, as shown in Table 1 below: To a third test tube, 15.6 mg. of 4-phenylazophenol allyl ether (a polymerizable yellow dye containing a polymerizable vinyl group) was added and an appropriate amount of the same monomer solution was added so that the yellow dye concentration was within the same range.

TABLE 1

| Example | Bondable Yellow Dye | mg. Dye | g. PEA/PEMA BDDA Formula | Dye Conc. Wt. % |
|---|---|---|---|---|
| 3 | Compound 1 | 10.45 | 10.0326 | 0.104 |
| 4 | Compound 2 | 9.67 | 9.0502 | 0.0966 |
| 5 | 4-phenylazophenol allyl ether | 15.6 | 15.0049 | 0.104 |

After dissolving each bondable yellow dye into the PEA/PEMA/BDDA monomer solution an amount of bis(4-tert-butylcyclohexylperoxy dicarbonate (Perkadox-16, AZKO Corp.) was added as the polymerization iniator (catalyst) to make the initiator concentration approximately 0.5%. One mm thick sheetstocks of the materials were made by placing the individual bondable yellow dye/monomer solutions via syringe into molds formed between two glass plates and a 1 mm Teflon gasket. The glass plates were held together with metal clips. Polymerization was effected by placing the molds into a 65° C. oven and curing for 17 hours. The temperature of the oven was raised to 100° C. and the mold heated for 3 hours to effect post-cure of the sheetstock. Rectangles measuring about 1×2 cm. were cut from the sheets and soxhlet extracted for 4–5 hours with acetone. Following extraction the material samples were dried in air followed by drying at about 50° C. under vacuum. The UV/visible transmission and absorption spectra was measured for each example listed in Table 1 both before and after soxhlet extraction and drying. From the absorbance of the samples at appropiate wavelengths between 400 and 500 nm, the percentage of the dye which is removed in soxhlet extraction was calculated for each example: Example 3=1%, Example 4=7% and Example 5=44%. The UV/visible transmission curves for the lens materials of Examples 3–5 (post-extraction) are shown in FIG. 1.

EXAMPLES 6-8

Dye Strength Comparison

The bondable yellow dye of Example 1 and one of the bondable yellow dyes of the Menikon Application, 2-[2'-methylphenylazo]-4-methyl-phenyl methacrylate ("Compound 3"), were weighed into test tubes according to the amounts listed in Table 2 below. An appropriate amount of a solution of monomers containing 66% PEA, 30.5% PEMA, and 3.3% BDDA by weight, was added to two of the test tubes to form the lens materials of Examples 6 and 8. The lens material of Example 7 was formed by adding an appropriate amount of the following solution of monomers: 65% PEA, 30% PEMA, 3.2% BDDA and 1.8% oMTP (a UV absorber).

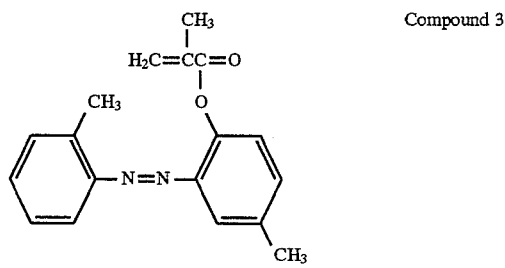

Compound 3

TABLE 2

| Example | Bondable Yellow Dye | mg. Dye | g. monomer solution | Dye Conc. Wt. % |
|---|---|---|---|---|
| 6 | Compound 3 | 16.4 | 9.9708 | 0.164 |
| 7 | Compound 3 | 40.7 | 9.9862 | 0.406 |
| 8 | Compound 1 | 14.78 | 10.0174 | 0.147 |

After dissolving each bondable yellow dye into the indicated monomer solution, an amount of bis(4-tert-butylcyclohexylperoxy dicarbonate) (Perkadox-16, AZKO Corp.) was added as the polymerization iniator (catalyst) to make the initiator concentration approximately 0.5% for Examples 6 and 8 and 1.0% for Example 7. One-mm thick sheetstocks of the materials were made by placing the individual bondable yellow dye/monomer solutions via syringe into molds formed between two glass plates and a 1 mm Teflon gasket. The glass plates were held together with metal clips. For Examples 6 and 7, polymerization was effected by placing the molds into a 65° C. oven and curing for 15–17 hours with a post-cure at 100° C. for 2–3 hours. Example 8 was cured at 65° C. for 1.5 hrs. with a post-cure at 100° C. for 2 hrs. Rectangles measuring approximately 1×2 cm. were cut from the sheets and Examples 6 and 8 were soxhlet extracted for 4–5 hours with acetone. Following extraction the material samples of Examples 6 and 8 were dried in air and then under vacuum at about 50° C. Example 7 was not extracted. The UV/visible transmission and absorption spectra for each example listed above in Table 2 am shown in FIG. 2.

Figure 2:
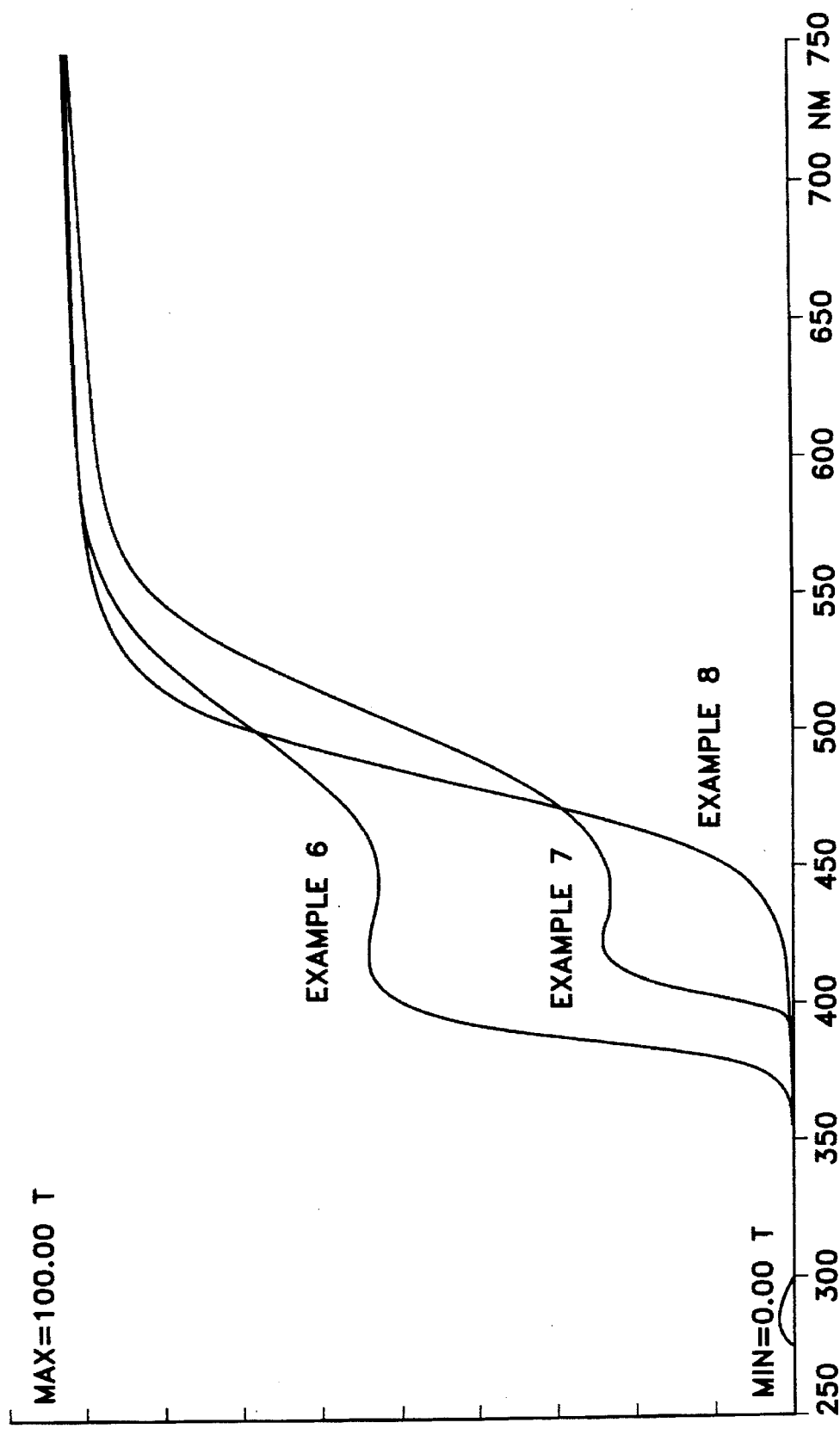

The dye strength of the yellow dyes in Examples 6–8 can be judged by comparing their transmission values at wavelengths in the blue light region, 400–500 nm. As shown in FIG. 2, Example 6 (0.164 wt. % of Compound 3) transmitted 53.1% at a wavelength of 450 nm. Example 7 (0.406 wt. % of Compound 3) transmitted 23.8% at this wavelength, and Example 8 (0.147 wt. % of Compound 1) transmitted only 8.3%.

Comparing Examples 6 and 8 which have approxiamately the same concentration of dye (0.164 wt. % vs. 0.147 wt. %). Compound 1 blocks almost 45% more light at 450 nm than does Compound 3.

Comparing Examples 7 and 8, Compound 1 blocks approximately 9t.7% of light at 450 nm while more than twice as much of the Compound 3 (0.147 wt. % vs. 0.406 wt. %) blocks only approximately 76.2%.

EXAMPLES 9-10

Preparation of Finished IOLs Containing Compounds 1 & 2.

The bondable yellow dyes of Examples 1 and 2 were weighed into individual test tubes. To each test tube an appropiate amount of a solution of monomers containing 65% PEA, 30% PEMA, 3.2% BDDA and 1.8% oMTP by weight to give a bondable yellow dye concentration of approximately 0.05 and 0.2% by weight respectively, as shown in Table 3 below:

TABLE 3

| Example | Bondable Yellow Dye | mg. Dye | g. monomer formula | Dye Conc. Wt. % |
|---------|---------------------|---------|--------------------|-----------------| 
| 9       | Compound 1          | 4.0     | 8.0326             | 0.0498          |
| 10      | Compound 2          | 92.4    | 47.3194            | 0.195           |

After dissolving the bondable yellow dye into the PEA/PEMA/BDDA/oMTP monomer formula an amount of bis (4-tert-butylcyclohexylperoxy dicarbonate (Perkadox-16, AZKO Corp.) was added as the polymerization initiator (catalyst) to make the initiator concentration approximately 1.8 wt. %. Lens optics of the materials were made by placing the individual bondable yellow dye/monomer solutions via syringe into polypropylene molds which formed lenses having a refractive power of 20 diopters with a central thickness of approximately 1 mm and a diameter of approximately 6 mm. For the samples of Example 9 the casting was performed on a plate assembly designed to hold up to 16 polypropylene lens molds held together between the plate and spring compressed metal dies so that as many as 16 lenses could be formed simutaneously. The samples of Example 10 were cast into lens molds and held together individually with metal clips. Polymerization was effected by placing the molds into a 80° C. oven and curing for 1 hour. The temperature of the oven was raised to 100° C. and the mold heated for 1 hour to effect pest-cure of the lenses. Following curing the polypropylene lens molds and optic were lathe cut to just less than the optic diameter to give an edge thickness of approximately 0.3 min. Short holes approximately 1 mm deep were drilled into opposite sides of the lens for haptic attachment. The lathed polypropylene lens molds and optic were cooled in a freezer at −5° C. for about 30 min. and then carefully split apart while still cold. The lens optics removed from the polypropylene molds were placed into individual tissue capsules. The lens optics were soxhlet extracted for 4–5 hours with acetone. Following extraction the material samples were dried in air followed by drying at about 50° C. under vacuum. Two haptics composed of a flexible plastic fiber material such as polypropylene (Prolane) or of a flexible plastiized nonofilament PMMA material were attached to the lens optic using the holes drilled on each side of the lens earlier to make a finished intraocular lens.

EXAMPLE 11

Preparation of Lens Material Containing Solvent Yellow 7

4-Phenylazophenol, [Solvent Yellow 7 (SY7)], a conventional yellow dye obtained from Aldrich Chemical Company in the amount of 10.3 mg was dissolved into a 10.01 g solution of monomers containing 66% PEA, 30.5% PEMA, and 3.3% BDDA by weight respectively giving a SY7 concentration of 0.103 wt %. After dissolving the SY7 into the monomer solution 52.3 mg of bis(4-tert-butylcyclohexylperoxy dicarbonate (Perkadox-16, AZKO Corp.) was added as the polymerization iniator (catalyst). One mm thick sheets were made by placing the SY7 monomer solution via syringe into a mold formed between two glass plates and a 1 mm Teflon gasket. The glass plates were held together with metal clips. Polymerization was effected by placing the mold into a 65° C. oven and curing for 17 hours. The temperature of the oven was raised to 100° C. and the mold heated for 3 hours to effect post-cure of the sheetstock. Approximately 1×2 cm. rectangles were cut from the sheet and the UV/visible measurements performed. The curve exhibited a strong attentuation of the short wavelengths of visible light in the 400 to 500 nm blue light region of the spectrum yielding a 50% transmission level at 473 nm. The rectangular samples were placed into individual tissue capsules and soxhlet extracted in acetone followed by drying in air then under vacuum at 50° C. Afterwards UV/visible measurements were performed again. The UV/visible transmission and absorption spectra were measured both before and after soxhlet extraction and drying. From the absorbance of the samples, at appropiate wavelengths between 400 and 500 rim, the percentage of the dye which is removed by soxhlet extraction was found to be 84%.

Figure 3:
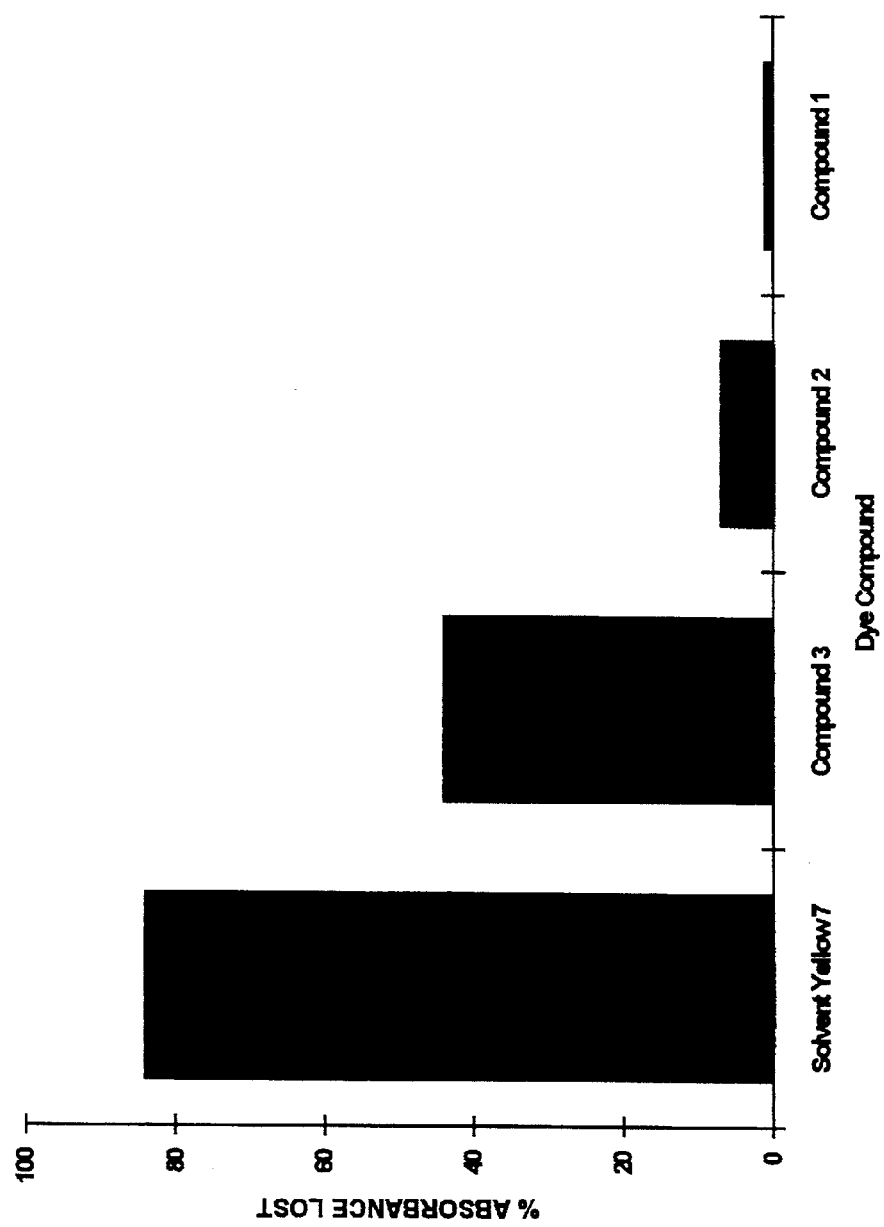
FIG. 3 presents a polymerization incorporation efficiency comparison of four dye compounds.

A comparison of the incorporation efficiency of the dyes of Examples 1, 2, 5 and 11 in the same lens material (66% PEA, 30.5% PEMA and 3.3% BDDA by weight) is shown in FIG. 3.

The amount of absorbance between 400–500 nm lost after extraction is an indication of the amount of dye removed from the lens material by the extraction process. Low absorbance loss for wavelengths between 400–500 nm indicates that very little dye failed to copolymerize with the lens forming monomers.

FIG. 3 shows that the largest loss of absorbance between 400–500 nm after extraction occurred with the Solvent Yellow 7 dye (84%). In contrast, the dyes containing polymerizable groups resulted in less than 50% absorption loss. Of the polymerizable dyes, 4-phenylazophenol allyl ether (containing a polymerizable vinyl group) resulted in a 44% absorbtion loss, while both Compounds 1 and 2 (containing polymerizable methacrylate groups) resulted in less than 10%. absorbtion loss. As measured by the absorption loss at appropriate wavelengths between 400–500 rim, the lens material containing Compound 2 lost approximately 7% of its blue light absorption while Compound 1 lost only 1%.

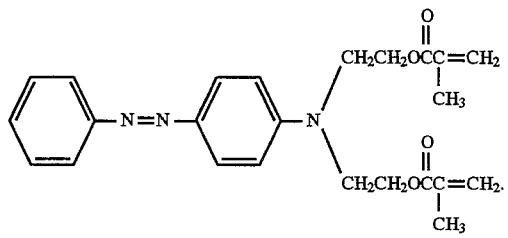

I claim:

1. A polymeric intraocular lens comprising:
   one or more monomers selected from the group consisting of acrylate and methacrylate monomers, and
   one or more polymerizable yellow dyes of the formula

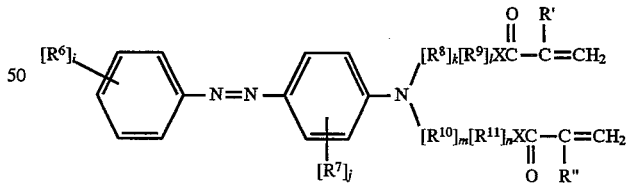

wherein

R' and R" independently=H or $CH_3$;

$R^6$ and $R^7$ independently=H, $C_1$ to $C_{20}$ alkyl, $OCH_3$, $OC_2H_5$, $OC_3H_7$, or $OC_4H_9$;

$R^8$, $R^9$, $R^{10}$ and $R^{11}$ independently=an acyclic organic spacing group of up to 10 atoms consisting of C, H, Si, O, N, P, S, Cl, Br or F, alone or in any combination;

i and j independently=the integer 1 or 2;

k and m independently=an integer from 1 to 6;

n and l independently=an integer from 0 to 6;

X=O, NH, $NR^5$;

$R^5=C_1$ to $C_{10}$ alkyl.

2. The lens of claim 1 wherein the total amount of yellow dye is less than about 1 wt %.

3. The lens of claim 2 wherein the total amount of yellow dye is less than about 0.25 wt %.

4. The lens material of claim 3 wherein the total amount of yellow dye is less than about 0.1 wt %.

5. The lens of claim 1 wherein the lens comprises one or more monomers selected from the group consisting of phenylethyl acrylate and phenylethyl methacrylate.

6. The lens of claim 1 further comprising an ultraviolet absorbing compound.

7. The lens of claim 6 wherein the total amount of polymerizable yellow dye and ultraviolet absorbing compound is less than about 1.9 wt. %.

8. The lens of claim 1 wherein the polymerizable yellow dye is